US007390621B2

(12) United States Patent
Li et al.

(10) Patent No.: US 7,390,621 B2
(45) Date of Patent: Jun. 24, 2008

(54) METHODS AND COMPOSITIONS FOR DETECTING TELOMERASE ACTIVITY

(75) Inventors: Zhunagwu Li, Clarksville, MD (US); Jun Bao, Hacienda Heights, CA (US); Hua Mao, Hacienda Heights, CA (US); Wenbin Ma, Frederick, MD (US); Lina Li, Germantown, MD (US)

(73) Assignee: Allied Biotech, Inc., Ijamsville, MD (US)

( * ) Notice: Subject to any disclaimer, the term of this patent is extended or adjusted under 35 U.S.C. 154(b) by 0 days.

(21) Appl. No.: 10/534,978

(22) PCT Filed: Nov. 12, 2003

(86) PCT No.: PCT/US03/35919

§ 371 (c)(1),
(2), (4) Date: Nov. 9, 2005

(87) PCT Pub. No.: WO2004/044246

PCT Pub. Date: May 27, 2004

(65) Prior Publication Data

US 2006/0246441 A1 Nov. 2, 2006

Related U.S. Application Data

(60) Provisional application No. 60/425,620, filed on Nov. 12, 2002.

(51) Int. Cl.
*C12Q 1/68* (2006.01)
*C12P 19/34* (2006.01)

(52) U.S. Cl. ............................ 435/6; 435/91.1; 435/91.2

(58) Field of Classification Search ........................ None
See application file for complete search history.

(56) References Cited

U.S. PATENT DOCUMENTS

| 5,629,154 A | 5/1997 | Kim et al. |
| 5,891,639 A | 4/1999 | Harley et al. |
| 6,221,584 B1 | 4/2001 | Emrich et al. |
| 6,391,554 B1 | 5/2002 | West et al. |

FOREIGN PATENT DOCUMENTS

GB WO 02/04488 A2 * 1/2002

OTHER PUBLICATIONS

Nakamura et al. Reduction of telomerase activity in human liver cancer cells by a histone deacetylase inhibitor. J. Cell. Physiol. (2001) 187:392-401.*
Elmore, Lynne W., Ph.D., et al., "Real-Time Quantitative Analysis of Telomerase Activity in Breast Tumor Specimens Using a Highly Specific and Sensitive Fluorescent-Based Assay", Diagnostic Molecular Pathology 11(3): 177-185, 2002.
Hou, Mi, et al., "Real-Time Quantitative Telomeric Repeat Amplification Protocol Assay for the Detection of Telomerase Activity", Clinical Chemistry 47:3, 519-524 (2001).
Uehara, Hiroshi, et al., "Detection of Telomerase Activity Utilizing Energy Transfer Primers: Comparison with Gel- and ELISA-Based Detection", BioTechniques 26:552-558 (Mar. 1999).
Seimiya, Hiroyuki, et al., "Telomere Shortening and Growth Inhibition of Human Cancer Cells by Novel Synthetic Telomerase Inhibitors MST-312, MST-295, and MST-199", Molecular Cancer Therapeutics, vol. 1, 657-665, Jul. 2002.
Burger, A.M., et al., "Inhibition of Telomerase Activity by Cisplatin in Human Testicular Cancer Cells", European Journal of Cancer, vol. 33, No. 4, pp. 638-644, 1997.
International Search Report issued Sep. 10, 2004 in counterpart foreign application under patent Cooperation Treaty (PCT) application No. PCT/US03/35919.
Wege, Henning, et al., "SYBR Green real-time telomeric repeat amplication protocol for the rapid quantification of telomerase activity", Nov. 2, 2002, Nucleic Acids Research, 2003, vol. 31, No. 2, e3, p.p. 1-7.

* cited by examiner

*Primary Examiner*—Kenneth R. Horlick
*Assistant Examiner*—David C Thomas
(74) *Attorney, Agent, or Firm*—Andrews Kurth LLP

(57) ABSTRACT

A method for determining telomerase activity using primer extension followed with real time PCR quantification is disclosed. The method of the present invention provides a rapid, sensitive and accurate measurement for telomerase activity in a biological sample. In one embodiment, the method includes the steps of: adding the biological sample to a reaction tube containing a first reaction mixture having a first primer and nucleoside triphosphates, a second reaction mixture having a second primer and a DNA polymerase, and a wax layer that separates the first reaction mixture from the second reaction mixture; incubating the biological sample with the first reaction mixture; admixing the extension product with the second reaction mixture; amplifying and quantifying the extension product using real-time PCR and a control template. In another embodiment, the detection method includes an in situ primer extension step that allows the production of the extension product within an intact cell. In this embodiment, the extension product can be preserved under appropriate conditions for an extended time before the completion of the quantification step.

15 Claims, 9 Drawing Sheets

Providing a reaction tube that contains a first reaction mixture having a first primer and deoxynucleoside triphosphates in a top portion of the tube, a second reaction mixture having a second primer and a DNA polymerase in a lower portion of the tube, and a layer of wax separating the first reaction mix from the second reaction mixture
102

↓

Adding a biological sample to the first reaction mixture and incubating the first reaction mixture under conditions suitable for a telomerase to produce an extension product from the first primer
104

↓

Elongating the extension product
106

↓

Admixing the extension product with the second reaction mixture by melting the wax layer
108

↓

Amplifying the extension product by real-time PCR
110

↓

Quantifying the amplified extension product using a control template
112

```
┌─────────────────────────────────────────────────────────────────┐
│  Introducing a first primer and nucleoside triphosphates into a │
│  sample cell                                                    │
│                                                             302 │
└─────────────────────────────────────────────────────────────────┘
                                 ↓
┌─────────────────────────────────────────────────────────────────┐
│  Incubating the sample cell under conditions suitable for the   │
│  telomerase within the sample cell to produce an extension      │
│  product from the first primer while maintaining the integrity  │
│  of the structure of the sample cell                            │
│                                                             304 │
└─────────────────────────────────────────────────────────────────┘
         │                       ↓
         │      ┌──────────────────────────────────────────┐
         │      │  Storing the sample cell under           │
         │      │  conditions that prevent degradation     │
         │      │  of the extension product                │
         │      │                                      306 │
         │      └──────────────────────────────────────────┘
         │                       ↓
         ↓                       ↓
┌─────────────────────────────────────────────────────────────────┐
│  Amplifying and quantifying the extension product using         │
│  real-time PCR                                                  │
│                                                             308 │
└─────────────────────────────────────────────────────────────────┘
```

A. 8,500 cells,  B. 2,500 cells,  C. 500 cells,  D. 100 cells
E. 20 cells,    F. 4 cells,      G. 1 cell,     H. Blank.

A. 300,000 molecules, B. 60,000 molecules, C. 12,000 molecules,
D. 2,400 molecules, E. 480 molecules, F. 100 molecules,
G. 20 molecules, H. Blank.

mo: Linear regression between TSR9 molecule number and threshold cycle,
cn: Linear regression between 293T cell number and threshold cycle.

A: syringe-treated cells incubated with TS prime;
C: untreated cells incubated with TS primer
E: blank.

B: syringe-treated cells incubated without TS primer;
D: untreated cells incubated without TS primer;

A; with TS primer, B: without TS primer, C: blank

METHODS AND COMPOSITIONS FOR DETECTING TELOMERASE ACTIVITY

CROSS REFERENCE TO RELATED APPLICATION(S)

This application claims the benefit of U.S. Provisional Patent Application Ser. No. 60/425,620, filed Nov. 12, 2002, the disclosure of which is hereby incorporated by reference.

TECHNICAL FIELD

The present invention generally relates to medical diagnostic and prognostic technology. In particular, the present invention relates to a method for the detection of telomerase activity.

BACKGROUND

Telomerase is an enzyme that synthesizes telomeres on chromosome ends. Telomeres are DNA sequences found at the ends of eukaryotic chromosomes which maintain the fidelity of genetic information during replication. Under normal circumstances, telomeres become shorter and shorter with each cycle of cell division. A sufficiently short telomere is believed to signal the cells to stop dividing.

Telomerase belongs to a class of enzymes known as reverse transcriptases that use RNA as a template for creating DNA. Telomerase contains both RNA and protein components. The RNA portion of the enzyme binds to the DNA in the telomere while the protein component lures DNA subunits into the region and attaches them to the end of the chromosome. Telomerase then elongates the G-rich strand of chromosomal termini by adding telomeric repeats. This elongation occurs by reverse transcription of a part of the telomerase RNA component, which contains a sequence complementary to the telomere repeat. Following telomerase-catalyzed extension of the G-rich strand, the complementary DNA strand of the telomere is presumably replicated by more conventional means. In the case of eukaryotic organisms, telomerases are composed of an accumulation of repeated defined nucleotide sequences (repeats) which, for example, contain the sequence TTAGGG in humans.

Telomerase activity is not detectable in normal tissues except germline cells. Germline cells, whose chromosomal ends must be maintained through repeated rounds of DNA replication, do not decrease their telomere length with time, presumably due to the activity of telomerase. Stem cells of renewing tissues express very low levels of telomerase and their telomeres shorten with multiple cell divisions. Telomerase activity is occasionally detected in tissues adjacent to tumors possibly reflecting the presence of occult micrometastases.

Telomerase is believed to have a role in the process of cell senescence. The repression of telomerase activity in somatic cells is likely to be important in controlling the number of times they divide. Indeed, the length of telomeres in primary fibroblasts correlates well with the number of divisions these cells can undergo before they senesce. The loss of telomeric DNA may signal to the cell the end of its replicative potential, as part of an overall mechanism by which multicellular organisms limit the proliferation of their cells.

Due to its role in controlling replication, telomerase has also recently been implicated in oncogenesis. Telomerase activity has been detected in most tumor cells. It has been suggested that telomerase is responsible for the unchecked growth of human cancer cells. Unlike normal cells, in cancer cells telomerase appears to grant the cell immortality by maintaining telomere length so that the cell never receives a signal to stop dividing. The telomerase enzyme is an ideal target for chemotherapy because this enzyme is active in about 90 percent of human tumors, but inactive in most normal cells. Pharmaceutical companies have screened thousands of compounds to find agents capable of blocking telomerase.

A method termed as telomeric repeat amplification protocol (TRAP) has been developed to measure telomerase activity. TRAP is based on the in vitro detection of the enzyme activity. Briefly, a synthetic oligonucleotide derived from the telomere sequence is used as a substrate. This substrate is elongated by the telomerase in a test sample and the elongation product is then amplified and quantified. Detailed description of the TRAP methods can be found in, for example, U.S. Pat. No. 5,891,639 to Harley et al. (hereinafter Harley) and U.S. Pat. No. 6,221,584 to Emrich et al. (hereinafter Emrich). Recently, a number of research groups have reported modified TRAP methods using real-time polymerase chain reaction (PCR) technology (See e.g., Hou et al., Clin. Chem. 47:519-524, 2001; Elmore et al., Diagn. Mol. Pathol., 11,177-185, 2002; and Wege et al., Nucleic Acids Res., 31:E3-3, 2003). Specifically, real-time PCR technology has been employed to provide a faster and more sensitive quantification of the elongation product of telomerase.

The current TRAPs typically include multiple incubation steps and transfer of sample from one tube to another after each incubation step. The transferring process is time consuming and prone to contamination and operation error (e.g., adding samples to a wrong tube or well). The current TRAPs usually start with a cell or tissue extract. Since telomerases, which contain both RNA and protein components, are subjected to the digestion of proteases and RNases in the extract, protease inhibitors and/or RNase inhibitors are often needed to prevent the degradation of the telomerases. Addition of protease inhibitors and/or RNase inhibitors to the extract increase the cost of the analysis. Thus, a need exists for an telomerase assay that is more flexible and can be performed easily and quickly at a low cost.

SUMMARY

A method for determining telomerase activity using primer extension followed with real-time PCR quantification is disclosed. The method provides a rapid, sensitive and accurate measurement for telomerase activity in a biological sample.

In one embodiment, the method includes the steps of: (1) adding the biological sample to a reaction tube containing a first reaction mixture having a first primer and nucleoside triphosphates, a second reaction mixture having a second primer and a DNA polymerase, and a wax layer that separates the first reaction mixture from the second reaction mixture; (2) incubating the biological sample with the first reaction mixture under conditions suitable for a telomerase to produce an extension product from the first primer; (3) admixing the extension product with the second reaction mixture; (4) amplifying the extension product using real-time PCR under conditions that allow the detection of telomerase activity from a single 293T cell; and (5) quantifying the amplified extension product using a control template that is amplified under the conditions in step (4). The single tube design of the embodiment simplifies the experimental procedure and reduces experimental error.

In another embodiment, the detection method includes the steps of: (1) introducing into a sample cell a first primer and nucleoside triphosphates; (2) incubating the sample cell under conditions suitable for a telomerase to produce an extension product from the first primer inside the cell (in situ primer extension); (3) amplifying the extension product using real-time PCR; and (4) quantifying the amplified extension product using a control template that is amplified under the conditions in step (3). In this embodiment, the extension product is produced within an intact sample cell and can be preserved under appropriate conditions for an extended time before the completion of the quantification step.

Also disclosed is a reagent kit for carrying out the method and for diagnosing telomerase-related diseases. In one embodiment, the reagent kit includes (1) reaction tubes that contain a first reaction mixture having a first primer and nucleoside triphosphates, a second reaction mixture having a second primer and a DNA polymerase, and a wax layer that separates the first reaction mixture from the second reaction mixture; and (2) control tubes or wells that contain a first reaction mixture having a first primer and nucleoside triphosphates, a second reaction mixture having a second primer, a DNA polymerase, and a control template, and a wax layer that separates the first reaction mixture from the second reaction mixture.

BRIEF DESCRIPTION OF DRAWINGS

The detailed description will refer to the following drawings, in which like numerals refer to like elements, and in which:

FIG. 1 is a schematic drawing depicting an embodiment of the method for detecting telomerase activity.

FIG. 3 is a schematic drawing depicting another embodiment of the method for detecting telomerase activity.

DETAILED DESCRIPTION

Figure 2:
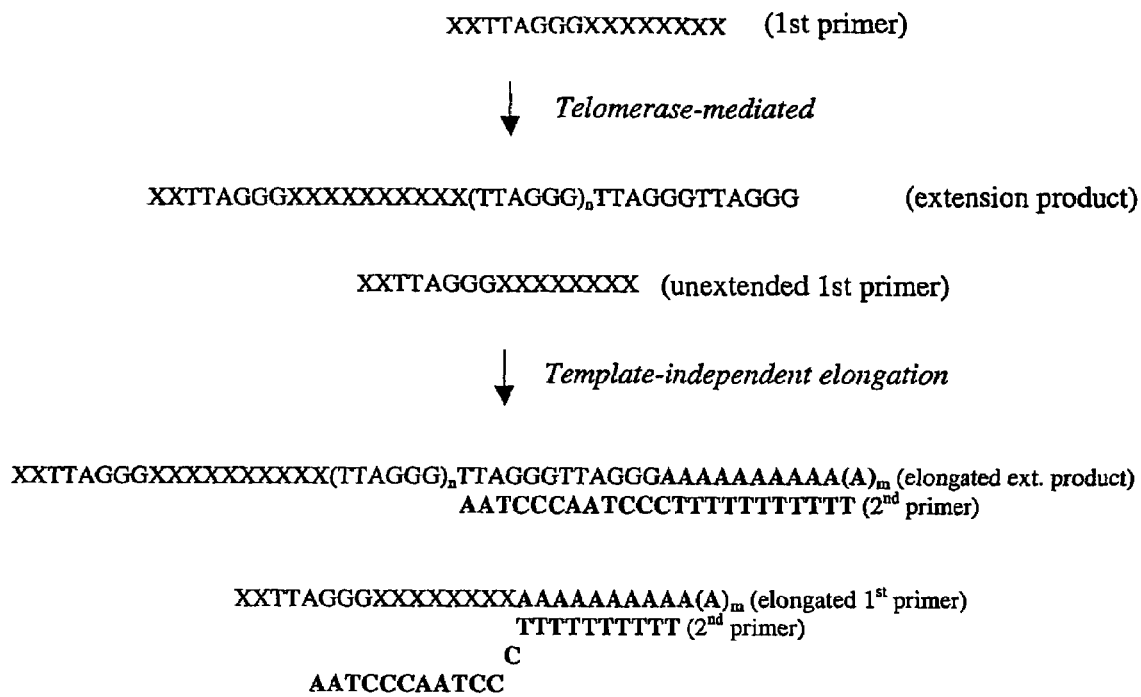
FIG. 2 is a schematic drawing depicting an additional extension step in the method for detecting telomerase activity.

FIG. 1 shows a method 100 for detecting and quantifying telomerase activity in a biological sample. First, the biological sample is added to a reaction tube that contains a first reaction mixture having a first primer and nucleoside triphosphates and a second reaction mixture having a second primer and a DNA polymerase (step 102). The first reaction mixture is separated from the second reaction mixture by a layer of wax that melts at high temperatures. The biological sample is mixed with the first reaction mixture, which occupies the top portion of the reaction tube, and incubated under conditions suitable for a telomerase to produce an extension product from the first primer (step 104). The extension product is then mixed with the second reaction mixture by melting the wax layer (step 108), and is amplified by real-time PCR (step 110). The unextended first primer in the first reaction mixture and the second primer in the second reaction mixture form the primer pair for PCR amplification. The telomerase activity in the biological sample is then quantified by comparing the amount of PCR product in the reaction tube to the amount of PCR product in control tubes having known amounts of a control template (step 112). In this embodiment, the experimental conditions for the first primer extension and the PCR reaction have been optimized to allow the detection of telomerase activity from a single 293T cell.

The biological sample includes tissues, cells and biological fluids isolated from a subject, as well as tissues, cells and biological fluids present within a subject. The biological sample also includes primary cells, transformed cells, and any other cultured cells. Since the method of the present invention detects the activity of telomerase, a RNase sensitive ribonucleoprotein, and not merely the presence of the RNA or protein components of telomerase, the method requires enzymatically active cell or tissue samples. In one embodiment, the biological sample is a tissue sample isolated by conventional means from a subject, e.g., a biopsy. Preferably, the biological sample is a cell or tissue extract, in particular an extract from human cells or tissues. The extract may be produced by repeated thawing/freezing of cells, by homogenizing cells or tissues, or by lysing cells or tissues in a lysis buffer containing a non-ionic or/and zwitterionic detergent. Examples of the non-ionic detergent include, but are not limited to, Tween 20, Triton X-100, Triton X-114, polydocanol (Thesit), NP-40, n-octylglucoside, n-dodecylglucoside, n-dodecyl-beta-D-maltoside, octanoyl-N-methylglucamide (MEGA-8), decanoyl-N-methylglucamide (MEGA-10), and isotridecyl-poly(ethyleneglycolether)$_n$. Examples of the zwitterionic detergents include, but are not limited to, CHAPS (3-[(3-cholamidopropyl)dimethylammonio]-1-propane-sulfonate), CHAPSO (3-[(3-cholamidopropyl)dimethyl-ammonio]-2-hydroxy-1-propane-sulfonate), N-dodecyl-N,N-dimethyl-3-ammonio-1-propane-sulfonate, and digitonin. The amount of detergent in the lysis buffer may vary from about 0.1% to about 2% by weight. In one embodiment, the lysis buffer contains about 0.5% detergent by weight.

Since telomerase contains both RNA and protein components, protease and/or RNase inhibitors may be added to the extract to prevent the destruction of telomerases in the extract by other cellular proteases. Examples of the protease inhibitors include, but are not limited to, amastain, 4-amidinophenylmethanesulfonyl fluoride (AMPSF), antipain, aprotinin, bestatin, chymostatin, cystatin, 3,4-dichloroisocoumarin, ebelactone A and B, elastatinal, ethylenediamine tetra-acetic acid (EDTA), ethylene glycol tetra acetic acid (EGTA), leupeptin, pepstatin A, phenylmethyl sulfonyl fluoride (PMSF), phosphoramidon, tosyl lysyl chloromethylketone (TLCK), tosyl phenylalanyl chloromethylketone (TPCK), and trypsin inhibitors. Examples of RNase inhibitors include, but are not limited to, pancreatic-type RNase inhibitors, human placenta RNase inhibitors, and diethyl pyrocarbonate (DEPC).

The reaction tube can be a container of any shape or size that fits the requirement of a particular application of the method. Typically, the reaction tube is a PCR tube or a PCR well as is well-known to one skilled in the art.

The first primer in the first reaction mix is an oligodeoxyribonucleotide suitable as a telomerase substrate. The first primer serves two functions: it serves as a substrate for the telomerase to produce an extension product, and it also serves as a primer in the subsequent PCR reaction. In one embodiment, the length of the first primer is 10-60 nucleotides. In another embodiment, the length of the first primer is 12-30 nucleotides. Preferably, the first primer, which serves as the telomerase substrate, does not contain a complete telomeric repeat sequence of the particular telomerase that will use the first primer as a substrate. For example, human telomerase adds telomeric repeats of sequence 5'-TTAGGG-3' (SEQ ID NO:1). Accordingly, if one is using the present method to assay for human telomerase activity, the telomerase substrate should be a human telomerase substrate lacking the complete repeat sequence 5'-TTAGGG-3'. The reason is that telomerase can extend the telomerase substrate only by the addition of telomeric repeats. Therefore, the second primer, which is to form a primer pair with the first primer in the PCR reaction, will necessarily comprise a sequence complementary to a telomeric repeat. If the first primer (i.e., the telomerase substrate) employed in the telomerase extension reaction comprises a complete telomeric repeat, then the second primer employed in the PCR reaction could hybridize readily to the unextended first primer and form primer-dimers that will potentially lead to negative PCR results.

The nucleoside triphosphates in the reaction mix include, but are not limited to, deoxydenosine triphosphate (dATP), deoxyguanosine triphosphate (dGTP), deoxyuridine triphosphate (dUTP), deoxythymidine triphosphate (dTTP) and deoxycytidine triphosphate (dCTP). In one embodiment, the reaction mixture contains dATP, dGTP, dCTP and one of dUTP and dTTP, in equal molar ratio. The nucleoside triphosphates are designated cllectively as dNTPs.

In addition to the first primer and the nucleoside triphosphates, the first reaction mixture may also contain a buffer system to maintain an optimal pH for the primer extension reaction for the telomerase. Examples of the buffer systems include, but are not limited to, phosphate buffer system, citrate buffer system, borate buffer system, Tris-(hydroxymethyl)aminomethane, 3-[(3-cholamidopropyl)dimethylammoniol]-1-propane ssulfonate (CHAPS), N-[2-hydroxyethyl]piperazine-N'-2-[ethanesulfaonic acid] (HEPES), and 3-[N-morpholino]propanesulfonic acid (MOPS).

The conditions suitable for a telomerase to produce an extension product from the first primer are well-known in the art. Typically, the telomer extension reaction is performed at about 20-30° C. for about 10-60 min, preferably at about 25° C. or about 30° C. for about 15-30 min, and most preferably at about 25° C. for about 20 min.

The extension product of the step 104 may be subjected to additional template-independent elongation (step 106). This elongation is preferably achieved by means of an enzymatic reaction e.g. by attaching nucleotides using terminal transferase or by ligation of short DNA fragments using DNA ligase. In one embodiment, a polyA tail is added to the 3' end of the extension product by terminal transferase. In another embodiment, a short DNA oligomer of 10-20 nucleotides is ligated to the 3' end of the extension product. These modifications generate a unique sequence for the second primer and thus allow the inclusion of the complete telomeric repeat sequence in the first primer. As shown in FIG. 2, a first primer containing a human telomeric repeat TTAGGG is used as a human telomerase substrate. After the telomerase-mediated extension, the extension product will have a 3' sequence of (TTAGGG)$_n$TTAGGGTTAGGG-3', where n is an integer that is equal to or is greater than zero. After the additional template-independent elongation that adds a polyA tail of at least 10 nucleotides to the 3' end of the extension product, the elongated extension product will have a 3' sequence of (TTAGGG)$_n$TTAGGGTTAGGGAAAAAAAAAA$_m$-3', where n is an integer that is equal to or is greater than zero.

The second primer can then be designed to have a sequence complementary to the junction of the telomeric repeat sequence; and the polyA sequence at the 3'-end of the elongated extension product. As shown in FIG. 2, a second primer complementary to the junction of the telomeric repeats and the additional nucleotides should be able to distinguish the unextended first primer from the extended product, so long as the first primer does not have a complete telomeric repeat sequence at its 3'-end.

In the absence of the additional elongation step 106, the second primer in the second reaction mixture typically contains multiple imperfect telomeric repeat sequences and at least one perfect telomeric repeat sequence to minimize the formation of non-specific PCR products such as primer-dimer.

The DNA polymerase in the second reaction mixture can be any DNA polymerase suitable for standard PCR conditions. Such enzymes are well-known to one skilled in the art. In an embodiment, the second reaction mixture also contains a magnesium salt that provides the optimal magnesium for the PCR amplification of the extension product. In another embodiment, the second reaction mixture also contains the first primer, or dNTP, or both.

The wax layer that separates the first reaction mixture from the second reaction mixture should have a melting temperature within the range of about 50-90° C., and preferably within the range of about 60-80° C. In an embodiment, a trace amount of a dye may be added to one of the first reaction mixture and the second reaction mixture to monitor possible leakage through the wax layer prior to the PCR amplification. In another embodiment, the second reaction mixture is premixed with the wax and are confined within the wax layer when the wax solidifies. The contents of the second reaction mixture are released when the way layer is melted at a higher temperature.

The extension product (with or without additional elongation) is quantified by the real-time PCR amplification. As is known to one skilled in the art, PCR amplification is typically achieved by adding a thermostable enzyme and a pair of primers to a reaction mixture containing a template and going through multiple thermocycles. In method 100, the unextended first primer in the first reaction mixture serves as the 5' PCR primer and the second primer in the second reaction mixture serves as the 3' PCR primer.

The PCR product in a real-time PCR reaction can be detected using fluorescence resonance energy transfer (FRET) technology. The accumulation of a specific PCR product can be measured by comparing the linear portion of each amplification to a standard curve generated using a known template.

In one embodiment, the PCR reaction is carried out normally but with the addition of a fluorescently labeled probe oligonucleotide that binds to a sequence between the two flanking PCR primers. The method relies on the 5' exonuclease activity of Taq polymerase to cleave a fluorescently labeled nucleotide from the 5' end of the probe. The probe oligonucleotide also has a fluorescent quencher at the 3' end that suppresses the overall fluorescence, therefore, when the 5' labeled nucleotide is removed the quenching effect is lost because the distance between the two fluorophores is too great to interfere with each other. Each cycle produces further increases in fluorescence allowing the whole PCR reaction to be followed in real time. The amount of template DNA present in the reaction can be calculated by comparing the linear part of the exponential amplification with a standard curve. Examples of such detection system include, but are not limited to, TaqMan® system (Applied Biosystems, Foster City, Calif.).

In another embodiment, the PCR product is detected by using single-labeled fluorogenic primers, such as the LUX® primers (Invitrogen, Carlsbad, Calif.) and Amplifluor RP® primers (Chemicon, Temecula, Calif.). The primers produce increased amount of fluorescence emission when the fluorogenic primer is incorporated into double-stranded PCR product. The amount of the PCR product then be determined based on the fluorescence produced during the amplification step of each PCR cycle in the closed reaction tube.

In yet another embodiment, the PCR product is detected using a fluorescent dye that binds preferentially to double-stranded DNA. The dye, such as SYBR® Green, can thus accurately quantitate the amount of double-stranded product made in the presence of single-stranded oligonucleotide primers.

The telomerase activity is quantified by comparing the increase of fluorescence in the reaction tube to the increase of fluorescence in a control tube that contains a known amount of a control template (step 110). Typically, real-time PCR is performed to generate a standard curve using a set of control tubes or wells that contain different dilutions of the control template. The extension product in the test tubes or wells are then amplified under identical PCR conditions and the telomerase activity in the test tubes or wells are quantified based on the standard curve. Telomerase activity is usually expressed as the amount of telomeric repeats synthesized within a certain period of time. A preferred control template for human telomerase is TSR9, which has the sequence of

```
5'-AATCCGTCGAGCAGAGTTAGGGTTAGGGTTAGGG  (SEQ ID NO:2)
TTAGGGTTAGGGTTAGGGTTAGGGTTAGGGTTAGGG
TTAG-3'.
```

In another embodiment, the cell or tissue extract is added to a master reaction mixture that contains the first primer, the second primer, dNTPs, a DNA polymerase, and a fluorescent dye that binds preferentially to double-stranded DNA. The telomerase-mediated extension and PCR amplification are performed consecutively in the same reaction tube.

FIG. 3 shows another method 300 for the detection of telomerase activity. In this embodiment, the primer extension step is performed within an intact cell. Specifically, the first primer and nucleoside triphosphates are introduced into an intact sample cell (step 302); the sample cell is then incubated under conditions suitable for the telomerase within the cell to produce an extension product from the first primer while maintaining the integrity of the cellular structure (step 304). The step 304 is also referred to as the "in situ primer extension step" because the extension product is generated inside the sample cell. The extension product is then amplified and quantified using real-time PCR and a control template (step 308). In one embodiment, the sample cell is mixed with the second reaction mixture and subjected to PCR amplification. In another embodiment, the sample cell is lysed in a lysis buffer and the lysate is used in the real-time PCR reaction.

Alternatively, the sample cell may be stored after the completion of the telomerase-mediated primer extension (step 306). In this embodiment, since the extension product is still within an intact sample cell, the extension product can be better preserved than the extension product generated with a cell/tissue extract. The method 300 thus allows an operator to perform the telomerase-mediated primer extension step immediately after receiving the sample, and store the intermediate product i.e., the sample cell after the primer extension step 304, for quantification at a later time.

The sample cells may be cultured in suspension or as a monolayer. The first primer and dNTPs may be introduced into cells using methods well-known to one skilled in the art. Examples include, but are not limited to, calcium phosphate precipitation, DEAE Dextran transfection, lipofectin/lipofectamin transfection, electroporation, microinjection, sonication, mechanical shearing (e.g., forcing cells through a syringe needle), and other chemical or physical means to disrupt the cell membrane or improve permeability of the cell membrane. In one embodiment, the cells are suspended and are forced to pass a 25-gauge needle at least once, preferably 2-5 times. The cells are then seeded into reaction tubes or wells in a culture medium containing the first primer and dNTPs. The shearing effect of passing through the needle damages the cell membrane and allows the first primer to enter the cells. The syringe-treated cells are then incubated with the first primer and dNTPs to allow the generation of the extension product by the telomerase in the cell.

In another embodiment, the first primer and dNTPs are introduced into cells using calcium phosphate precipitation. The calcium phosphate precipitation is formed in the presence of the first primer and dNTP, and is added to the cells. The cells are then incubated at 37° C. for about 10-120 min to allow the generation of the extension product by the telomerase in the cell.

The methods of the present invention may be used as diagnostic assays to determine the progression or severity of a telomerase-related disease such as Hodgkin's disease. The quantification of telomerase activity is also useful, for example, to determine the severity of the telomerase-related disease following treatment.

The detection methods described herein may be performed, for example, by utilizing prepackaged diagnostic kits containing an extension composition containing a first primer and nucleoside triphosphates, and a detection composition containing a second primer, nucleoside triphosphates, a double-stranded DNA binding dye, and a DNA polymerase. The extension composition is capable of producing an extension product from the first primer when mixed with a telomerase; and the detection composition is capable of amplifying the extension product in a PCR reaction and generating a labeled amplification product for quantification. The diagnostic kits may be conveniently used, e.g., in clinical settings to diagnose subjects exhibiting symptoms or family history of a telomerase-related disease such as Hodgkin's disease. Any cell type or tissue in which telomerase is expressed may be utilized in the prognostic or diagnostic assays described herein.

In one embodiment, the telomerase activity in a biological sample is determined and an increased telomerase activity over a pre-determined normal level indicates a telomerase-related disease such as Hodgkin's disease.

The detection method described herein can also be utilized as a prognostic assay to identify subjects having or at risk of developing telomerase-related disease, such as Hodgkin's disease, that is associated with aberrant telomerase activity.

Furthermore, the prognostic assay described herein can be used to determine whether a subject can be administered a drug candidate to treat or prevent a disease associated with aberrant telomerase activity. Thus, the present invention provides methods for determining whether a subject can be effectively treated with an agent for a disease associated with aberrant telomerase activity. Prognostic assays can be devised to determine whether a subject undergoing treatment for a telomerase-related disease has a poor outlook for long term survival or disease progression. By establishing telomerase activity profiles of different stages of the disease, from onset to later stages, an activity pattern may emerge to correlate a particular activity profile to increased likelihood of a poor prognosis. The prognosis may then be used to devise a more aggressive treatment program and enhance the likelihood of long-term survival and well-being. Similarly, the detection method of the present invention can be used in basic drug screening or clinical trials to monitor the influence of agents (e.g., drugs, small molecules, proteins, nucleotides) on the activity of telomerase. For example, the effectiveness of an agent determined by a screening assay to decrease telomerase activity, can be monitored in clinical trials of subjects exhibiting increased telomerase activity. In such clinical trials, the activity of telomerase can be used as a "read-out" of the phenotype of a particular tissue.

In an embodiment, the present invention provides a method for monitoring the effectiveness of treatment of a subject with an agent including the steps of (i) obtaining a pre-administration sample from the subject prior to administration of the agent; (ii) detecting the level of telomerase activity in the pre-administration sample; (iii) obtaining one or more post-administration samples from the subject; (iv) detecting the level of telomerase activity in the post-administration samples; (v) comparing the level of telomerase activity in the pre-administration sample with the level of telomerase activity in the post-administration sample or samples; and (vi) altering the administration of the agent to the subject accordingly. For example, decreased administration of the agent may be desirable to increase the activity of telomerase to higher levels than detected, i.e., to decrease the effectiveness of the agent. According to such an embodiment, telomerase activity may be used as an indicator of the effectiveness of an agent, even in the absence of an observable phenotypic response.

As described herein, the telomerase detection method may be used for a variety of applications, including but are not limited to, evaluating the effectiveness of telomerase inhibitors, measuring the relationship between telomerase activity and cell culture conditions, determining the relationship between telomerase activity and aging, or between telomerase activity and tumorigenesis, diagnosing telomerase-related disease, and monitoring the treatment for such diseases.

EXAMPLES

Example 1

Determination of Primer Ratio 293T cell line (primary human embryonal kidney transformed by sheared human adenovirus type 5 (Ad 5) DNA and SV 40 T-antigen, obtained from American Type Culture Collection) was cultured in Dulbecco's modified Eagle's medium (DMEM) with 10% fetal bovine serum (FBS) at 37° C. in a humidified incubator with 5% $CO_2$. The cells were collected at 70-85% confluency, counted, and lysed using a lysis buffer containing 10 mM Tris-HCl, pH7.5, 1 mM $MgCl_2$, 1 mM EGTA, 0.1 mM Benzamidine, 5 mM b-mercaptoethanol, 0.5% w/v CHAPS, and 10% w/v Glycerol (CHAPS lysis buffer) on ice for 30 min. The protein concentration was determined using the BCA Protein Assay Kit (Pierce, Rockford, Ill.). The cell extract was stored at –70° C.

Oligonucleotide primers were ordered from Integrated DNA Technologies, Inc. (Coralville, Iowa). The first primer (FP) has the sequence of 5'-AATCCGTCGAGCAGAGTT-3' (SEQ ID NO:3) and is designated TS, the second primer (SP) has the sequence of 5'-GCGCGGCTTACCCTTACCCTTAC-CCTAACC-3' (SEQ ID NO:4) and is designated ACX. To test the effect of primer ratio of the first primer versus the second primer, different ratios (FP:SP=1:1, 1:08, 1:0.5, and 1:0.2) were used. Briefly, 1, μl of cell extract at different dilutions was mixed with 1 μl of the primer mixture (0.5 μg TS/ACX at different ratio), 11.5 μl water, and 12.5 μl PCR premix buffer containing 0.25 unit DNA Polymerase, 2.5 mM of dATP, dUTP, dCTP and dGTP, and SYBR Green (1:2000 dilution of the SYBR Green 1 stock solution (S-7563) purchased from Molecular Probes Inc., Eugene, Oreg.), incubated first at 25° C. for 20 nm and then at 95° C. for 10 min, and amplified by quantitative real time PCR (95° C. 30 sec, 60° C. 30 sec, 72° C. 30 sec for 40 cycles). The result indicated that the ratio 1/1 (w/w) gave the best result (Table 1).

TABLE 1

Effect of primer ratio on quantitative real time PCR reaction

| | | Threshold cycles ($C_T$) FP/SP ratio | | | |
|---|---|---|---|---|---|
| Dilutions | Cell Extract (μg) | 1/1 | 1/0.8 | 1/0.5 | 1/0.2 |
| A | 0.40 | 20.7 | 25.4 | 28.2 | 27.5 |
| B | 0.08 | 22.5 | 27.0 | 26.9 | 27.9 |
| C | 0.016 | 25.1 | 27.8 | 28.4 | 30.1 |
| D | 0.0032 | 27.4 | 30.0 | 32.3 | 32.7 |
| E | 0.00064 | 29.6 | 32.0 | 31.2 | 35.4 |
| F | 0.00013 | 32.4 | 33.8 | 35.6 | 35.4 |
| Blank | — | 33.0 | 33.5 | 34.3 | — |

Example 2

Determination of Assay Sensitivity

Figure 4A:
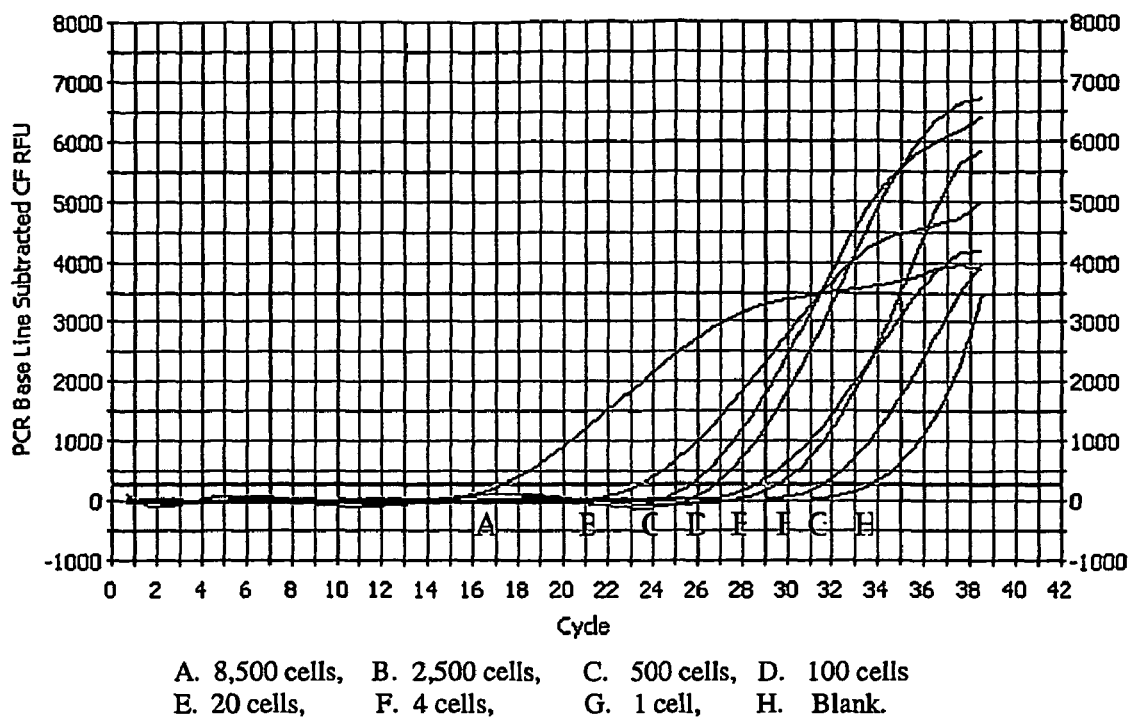
FIGS. 4A and 4B are a fluorescence/PCR cycle plot and a threshold cycle/cell number plot, respectively, that demonstrate the sensitivity of the detection method.
Figure 4B:
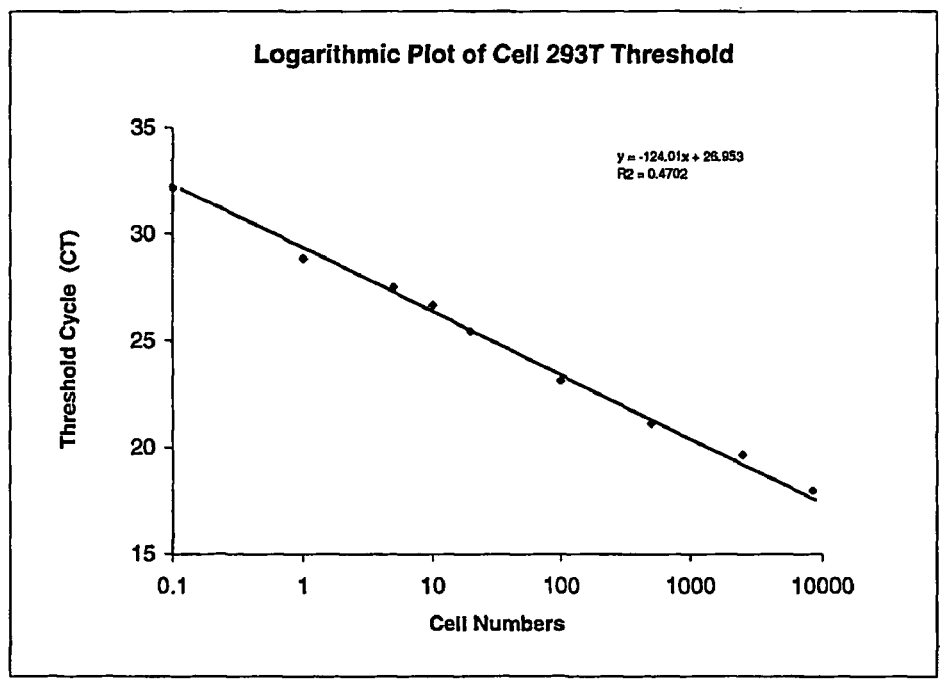

To test the sensitivity of the telomerase activity assay method, the assay was performed using different amounts (or cell numbers) of 293T cell extract under the conditions described in Example 1 and a FP/SP ratio of 1/1. As shown in Table 2 and FIG. 4, the method is capable of detecting telomerase activity from a single 293T cell.

TABLE 2

Detection of telomerase activity in 293T cells

| | Cell Extract (Per reaction) | | Threshold cycles ($C_T$) |
|---|---|---|---|
| Dilutions | μg | Cell | Numbers |
| A | 2.800 | 8500 | 18.0 |
| B | 0.82 | 2500 | 19.7 |
| C | 0.16 | 500 | 21.1 |
| D | 0.032 | 100 | 23.1 |
| E | 0.0064 | 20 | 25.4 |
| F | 0.0032 | 10 | 26.6 |
| G | 0.0016 | 5 | 27.5 |
| H | 0.00033 | 1 | 28.8 |
| Blank | — | — | 33.0 |

Example 3

Generation of Standard Curves

Figure 5A:
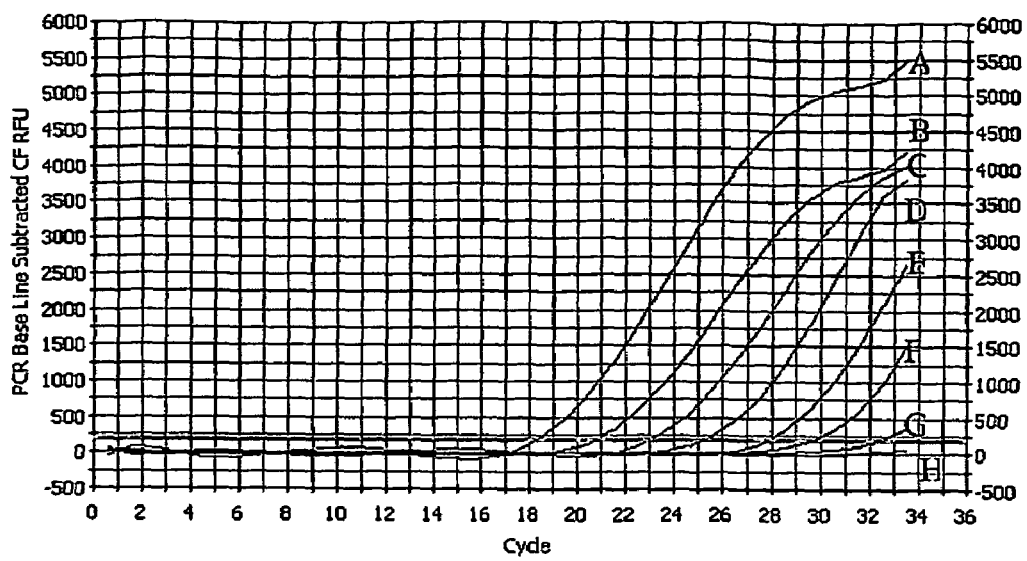
FIGS. 5A and 5B are a fluorescence/PCR cycle plot and a threshold cycle/template molecule number plot, respectively, generated by real-time PCR using a control template.
Figure 5B:
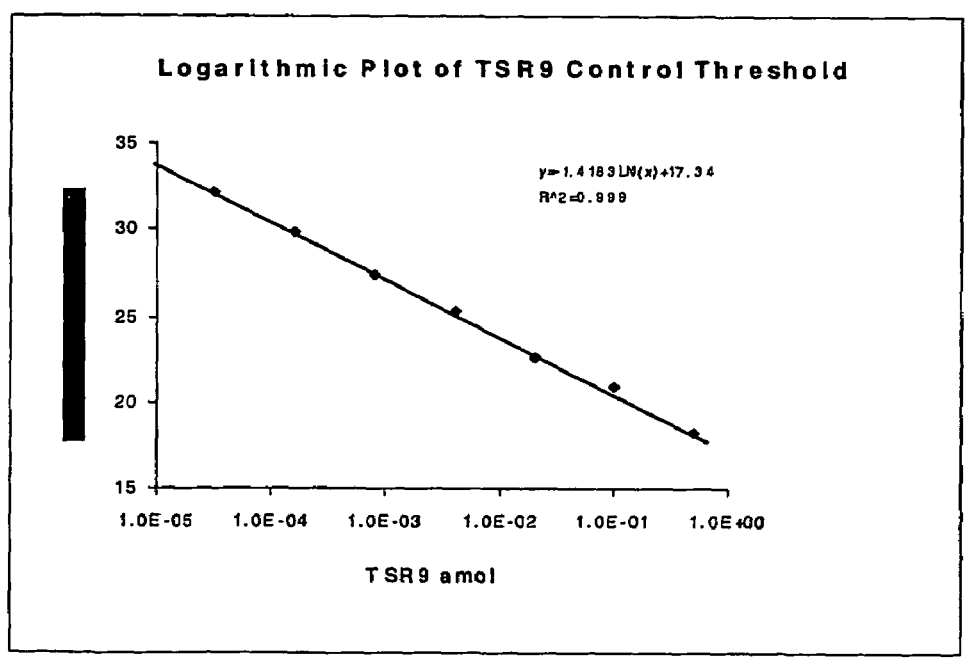
Figure 6:
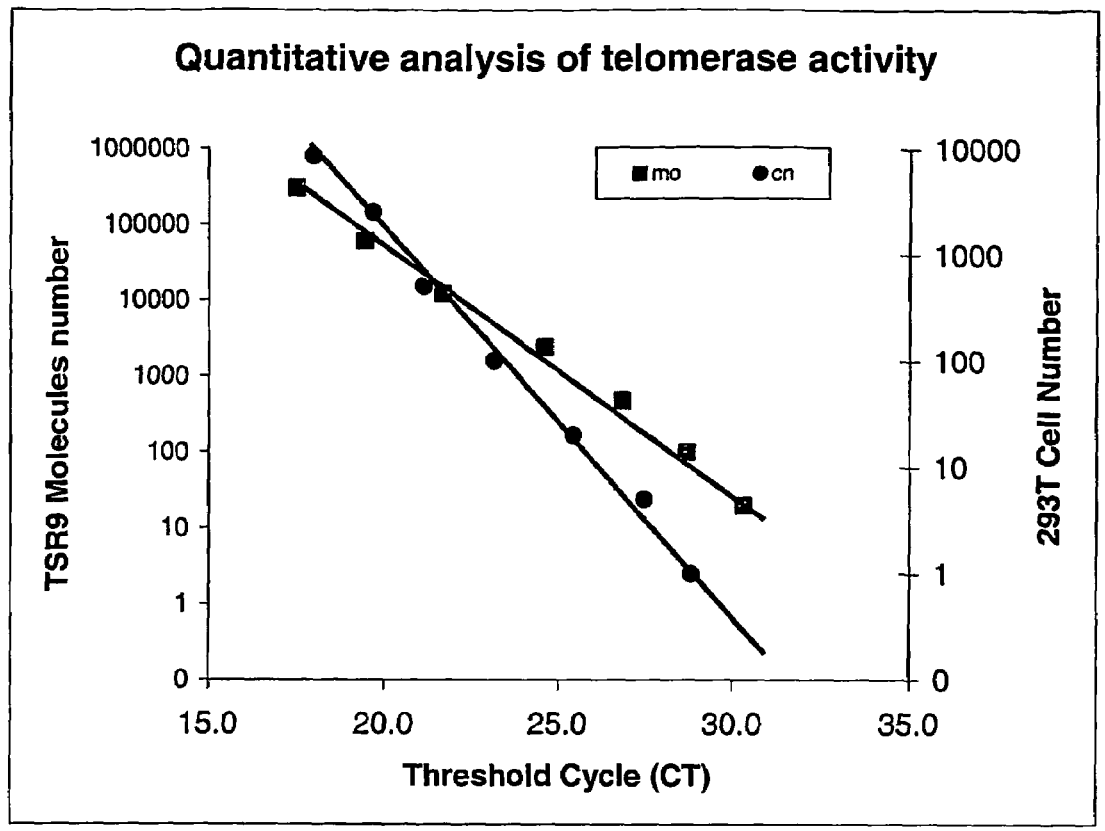
FIG. 6 is a plot showing linear regression between sample cell number and threshold cycle or between template molecule number and threshold cycle.

To quantify the results from real time PCR reaction, a control template molecule was used to generate a standard curve under conditions described in Example 2 to correlate telomerase activity with template molecule numbers per reaction through the threshold cycles. As shown in Table 3 and FIG. 5, the standard curve was generated using the reading of the threshold ($C_T$) of the real-time PCR under the standard reaction conditions and a control template TSR9. FIG. 6 shows the liner regression between 293T cell number and threshold cycle and liner regression between the control template TSR9 molecule number and threshold cycle.

TABLE 3

Generation of the standard curve using TSR9 template control

| | TSR9 concentration | | |
|---|---|---|---|
| Dilutions | (μg/μl) | molecules/reaction | Threshold cycles ($C_T$) |
| S1 | 0.5 | 300000 | 18.3 |
| S2 | 0.1 | 60000 | 20.8 |
| S3 | 0.02 | 12000 | 22.6 |
| S4 | 0.004 | 2400 | 25.2 |
| S5 | 0.0008 | 480 | 27.3 |
| S6 | 0.00016 | 96 | 29.8 |
| S7 | 0.000032 | 20 | 32.0 |
| S8 | 0.0000064 | 4 | 32.5 |
| Blank | — | — | 33.0 |

Example 4

Specificity of the Telomerase Assay Method

Figure 7:
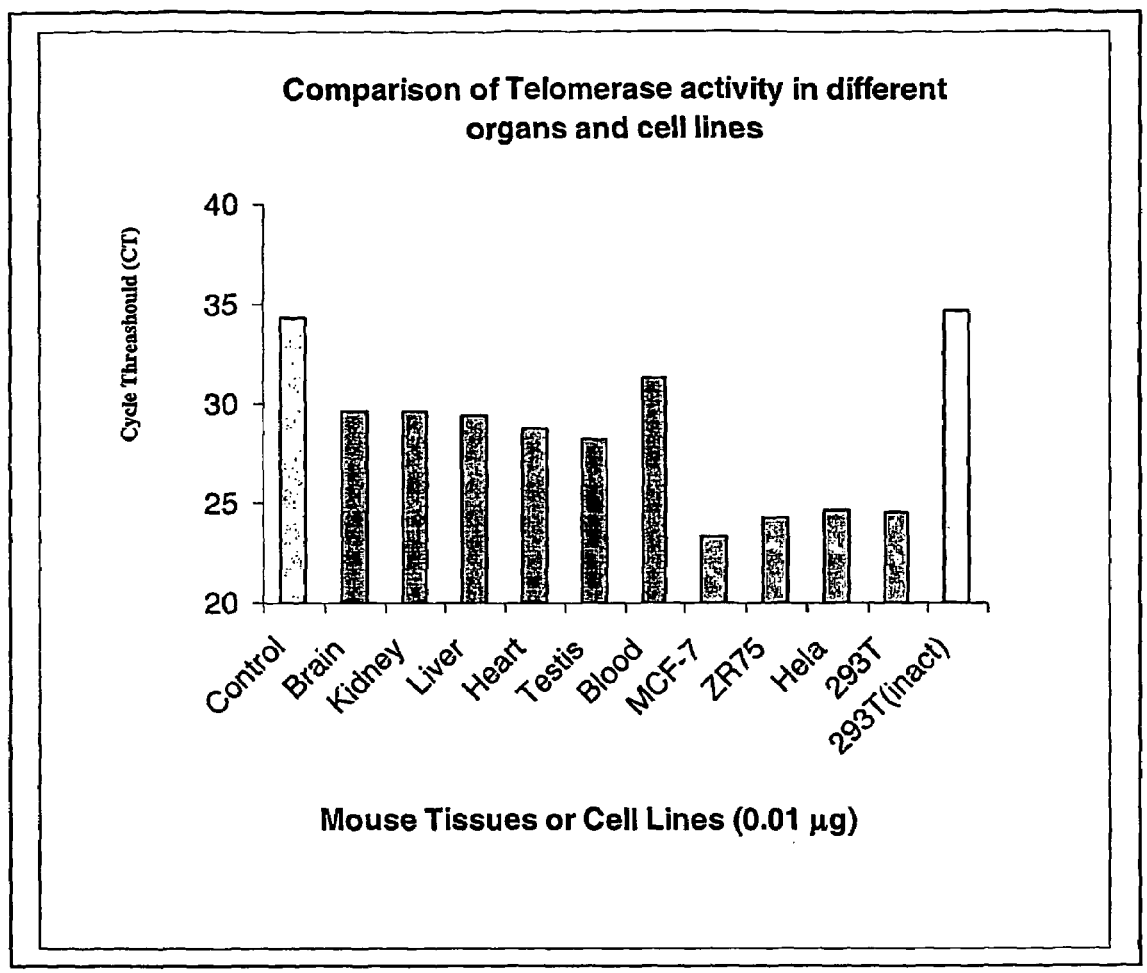
FIG. 7 is a bar plot showing telomerase activity in various cell lines and tissues

To test the specificity of the telomerase assay method, the assay was performed using several tumor cell lines including MCF7 (breast pleural effusion adenocarcinoma), ZR-75-1 (breast ascites ductal carcinoma) and Hela (cervix adenocarcinoma) cells, various murine tissues (harvested from adult C57BL/6 mice) including brain, kidney, liver, heart, testis, and blood, as well as heat inactivated (95° C. for 10 min) extract from 293T cells. As shown in Table 4 and FIG. 7, telomerase activity is detected in proliferating cells, cancer cell lines, (293T, Hela, MCF7 and ZR-75-1), but is not detected in heat inactivated 293T cell extract and blank control. The results also indicated that there was low telomerase activity in normal adult murine tissues, indicating that the proliferating cells (e.g., stem cells) in normal tissues are detectable.

TABLE 4

Telomerase activity in various cell lines and murine tissues

| Sample | Cell Extract (Per reaction) μg | Cycle Thresholds ($C_T$) Mean ± SD |
|---|---|---|
| Control | — | 34.3 ± 0.2 |
| Brain | 0.01 | 29.6 ± 0.2 |
| Kidney | 0.01 | 29.6 ± 0.2 |
| Liver | 0.01 | 29.4 ± 0.2 |
| Heart | 0.01 | 28.6 ± 0.2 |
| Testes | 0.01 | 28.2 ± 0.2 |
| Blood | 0.01 | 31.3 ± 0.1 |
| MCF7 | 0.01 | 23.3 ± 0.5 |
| ZR75 | 0.01 | 24.2 ± 0.4 |
| Hela | 0.01 | 24.6 ± 0.4 |
| 293T | 0.01 | 24.3 ± 0.5 |
| 293T (heat inactivated) | 0.01 | 34.7 ± 0.2 |

Example 5

Stability of the Reaction Mixture

To test the stability of the reagents used in the telomerase assay, a reaction mixture containing a first primer TS, DNA Polymerase, dNTPs and SYBR Green was prepared. Aliquots of the reaction mixture were kept at room temperature for 0, 24, 48 or 72 h, and tested in a telomerase assay. As shown in Table 5, the reaction mixture seems to be stable at room temperature for up to at least 72 hours.

TABLE 5

Stability of the reaction mixture at room temperature

| | | Threshold cycles ($C_T$) Exposure at RT (hrs) | | | |
|---|---|---|---|---|---|
| Dilutions | Cell Extract (μg) | 0 | 24 | 48 | 72 |
| A | 2.0 | 18.0 | 16.7 | 18.2 | 16.4 |
| B | 0.40 | 21.6 | 22.4 | 21.9 | 20.9 |
| C | 0.08 | 22.3 | 21.8 | 21.9 | 21.4 |
| D | 0.016 | 24.3 | 24.2 | 23.9 | 24.2 |
| F | 0.0032 | 26.1 | 25.7 | 25.6 | 25.2 |
| G | 0.00064 | 27.9 | 27.7 | 28.2 | 27.6 |
| H | 0.00013 | 28.3 | 28.4 | 28.6 | 31.5 |
| Blank | — | 34.3 | 32.1 | 33.9 | 32.9 |

Example 6

Primer Extension in Intact Cells 293T cells were cultured in growth medium (Dulbecco's modified Eagle's medium (DMEM) with 10% fetal bovine serum (FBS) at 37° C. in a humidified incubator with 5% $CO_2$). The cells were trypsinized, washed with the growth medium, suspended in the growth medium at a density of $1 \times 10^6$ cells/ml, and subjected to one of the following treatment:

Treatment A: The cell suspension was transferred to a sterile centrifuge tube, centrifuged at 800 rpm for 5 min in a Beckman GS-6R centrifuge, re-suspended in phosphate buffered saline (PBS). The re-suspended cells were drawn up in a sterile 1-ml syringe through a 25-gauge needle and then expelled by steady pressure on the plunger. The syringe procedure was repeated five times. The cells were transferred into sterile centrifuge tubes at $1 \times 10^4$ cells/tube and a transfer medium (2.5 mM dNTP and 0.1% bovine serum albumin (BSA)) was added, either with or without TS primer. The cells were cultured at 37° C. for 60 min. The tubes were centrifuged at 4° C. for 20 min. and suspensions were collected. The pallets were lysated using Chaps buffer at 40° C. for 30 min. The lysates were centrifuged at 14,000 rpm for 20 min at 4° C. The supernatants were collected, heated at 95° C. for 10 min, and stored at −70° C. before use.

Alternatively, the cells may be seated in 96 well plates at a density of $1 \times 10^4$ cells/well after the syringe procedure and cultured overnight at 37° C. in a humidified incubator with 5% $CO_2$. The next day, the cells may be washed with PBS and a desired amount of transfer buffer (PBS with TS primer, 0.5 μg/well, dNTP 2.5 mM and 0.1% BSA; or PBS with dNTP, 2.5 mM and 0.1% BSA, or PBS only) is added to each well. After incubation at 37° C. for 30 min, 60 min, and overnight, the cells are collected and lysated with the CHAPS buffer at 4° C. for 30 min. The lysates are centrifuged at 14,000 rpm. The supernatants are collected, heated at 95° C. for 10 min, and stored at −70° C. before use.

Treatment B: The cell suspension was directly seeded in a 96-well plate, cultured overnight, and transfected with a desired amount of TS primer and dNTP using calcium phosphate precipitation. Briefly, the 293T cells grew in growth medium (DMEM with 10% FBS) overnight. The growth medium was replaced with fresh growth medium 3 hours before the transfection. Calcium phosphate precipitation (using the Calcium phosphate kit from GIBCO) was formed in the presence of the TS primer and dNTP (HBS 100 ul, phospate 2 ul, $H_2O$ 26 ul, carrier DNA 10 ul, first primer 20 ul, 0.25 mM dNTP, 12 ul calcium) and added to the cells. The cells were incubated at 37° C. for 10, 30, and 60 min, and were lysed with CHAPS lysis buffer at 4° C. for 30 min. The lysates were heated at 100° C. for 10 min and centrifuged at 14,000 rpm for 20 min. The supernatants were collected and stored at −70° C.

Figure 8:
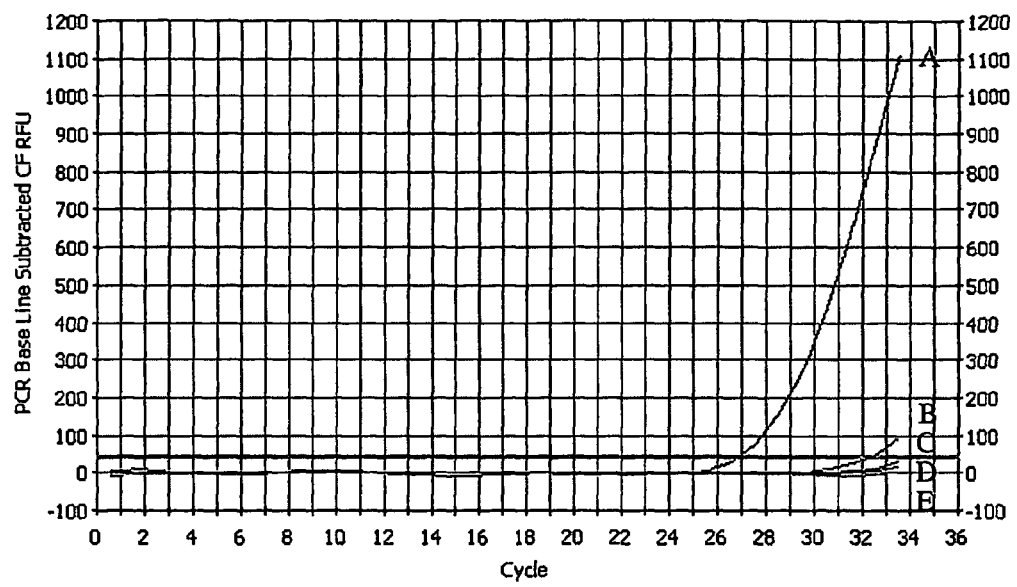
FIG. 8 is a fluorescence/PCR cycle plot showing the detection of telomerase activity in cells subjected to in situ primer extension after syringe treatment.
Figure 9:
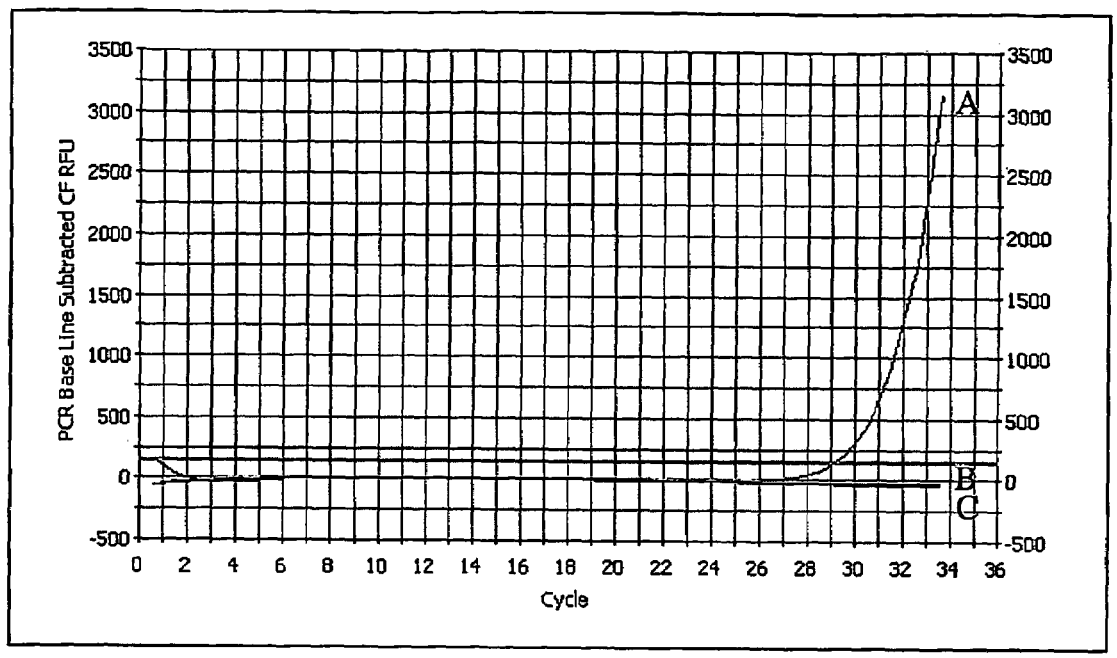
FIG. 9 is a fluorescence/PCR cycle plot showing the detection of telomerase activity in cells subjected to in situ primer extension after calcium phosphate precipitation.

One microliter of the lysate from treatment A or B was mixed with 11.5 μl water and 12.5 μl premix containing dNTPs (2.5 mM for each nucleoside triphosphate), 0.25 unit of DNA polymerase, 0.25 μg ACX primer, and subjected to quantitative real-time PCR (95° C. for 10 min, 95° C. 30 sec, 60° C. 30 sec, 72° C. 30 sec for 35-40 cycles). The results shown in FIG. 8 indicate that telomerase activity is detectable in 293T cells after an one hour incubation with the TS primer and dNTP as described in treatment A. The results shown in FIG. 9 indicate that telomerase activity is detectable in 293T cells after a 30-minute incubation with calcium phosphate precipitate containing the TS primer and dNTP, as described in treatment B. No telomerase activity was detected without the TS primer, suggesting that the products detected are telomerase specific.

Although preferred embodiments and their advantages have been described in detail, various changes, substitutions and alterations can be made herein without departing from the scope of the compositions and methods as defined by the appended claims and their equivalents and all such are intended to be within the scope of the appended claims.

What is claimed is:

1. A method for detecting and quantifying telomerase activity in a biological sample, the method comprising the steps of:
   adding the biological sample to a reaction tube comprising:
      a first reaction mixture comprising a first primer, and nucleoside triphosphates;
      a second reaction mixture comprising a second primer and a DNA polymerase; and
      a wax layer separating the first reaction mixture from the second reaction mixture in the reaction tube;
   incubating the biological sample with the first reaction mixture under conditions suitable for a telomerase to produce an extension product from the first primer, said extension product having a telomeric repeat sequence at a 3' end;
   elongating the extension product at the 3' end by template-independent polyadenylation or template-independent ligation;
   admixing the extension product with the second reaction mixture by melting the wax layer;
   amplifying the elongated extension product using a real-time polymerase chain reaction under conditions that allow the detection of telomerase activity from a single 293T cell; and
   quantifying the amplified extension product using a control template.

2. The method of claim 1, wherein the biological sample is added in the form of a cell or tissue extract.

3. The method of claim 1, wherein the real-time polymerase chain reaction is quantified by using a fluorescently labeled probe oligonucleotide that binds to a sequence between the first and the second primers.

4. The method of claim 1, wherein the real-time polymerase chain reaction is performed in the presence of a fluorescent dye that binds preferentially to double-stranded DNA.

5. The method of claim 1, wherein said second primer comprises a sequence complementary to a junction of the telomeric repeat sequence and the polyadenylate sequence at the 3' end of the extension product, and wherein the second primer is a single-labeled fluorogenic primer that produces an increased amount of fluorescence emission when the fluorogenic primer is incorporated into double-stranded polymerase chain reaction product.

6. The method of claim 1, wherein the control template has a nucleotide sequence recited in SEQ ID NO:2.

7. A method for detecting and quantifying telomerase activity in a sample cell, the method comprising the steps of:
   suspending the sample cell in a cell suspension;
   passing the cell suspension through a needle 2-5 times;
   introducing into a sample cell a first primer and nucleoside triphosphates;
   incubating the sample cell under conditions suitable for a telomerase to produce an extension product from the first primer; said extension product having a telomeric repeat sequence at a 3' end,
   adding a polyadenylate sequence to the 3' end of the extension product by template-independent polyadenylation or template-independent ligation;
   amplifying the polyadenylated extension product using real-time polymerase chain reaction in the presence of a second primer that comprises a sequence complementary to a junction of the telomeric repeat sequence and the polyadenylate sequence at the 3' end of the polyadenylated extension product; and
   quantifying the amplified extension product using a control template.

8. The method of claim 7, further comprising: lysing the sample cell with a lysis buffer.

9. The method of claim 7, wherein the first primer and nucleoside triphosphates are introduced into the sample cell by calcium phosphate precipitation.

10. The method of claim 7, wherein the real-time polymerase chain reaction is performed in the presence of a fluorescent dye that binds preferentially to double-stranded DNA.

11. The method of claim 7, wherein the second primer is a fluorogenic primer that produces an increased amount of fluorescence emission when the fluorogenic primer is incorporated into double-stranded polymerase chain reaction product.

12. The method of claim 7, wherein the control template has a nucleotide sequence recited in SEQ ID NO:2.

13. A method for detecting and quantifying telomerase activity in a biological sample, the method comprising the steps of:
   adding the biological sample to a reaction tube comprising:
      a first reaction mixture comprising a first primer and nucleoside triphosphates;
      a second reaction mixture comprising a second primer and a DNA polymerase; and
      a wax layer separating the first reaction mixture from the second reaction mixture in the reaction tube;
   incubating the biological sample with the first reaction mixture under conditions suitable for a telomerase to produce an extension product from the first primer, said extension product;
   elongating the extended product at a 3' end by template-independent polyadenylation;
   admixing the extension product with the second reaction mixture by melting the wax layer;
   amplifying the extension product using a real-time polymerase chain reaction under conditions that allow the detection of telomerase activity from a single 293T cell; and
   quantifying the amplified extension product using a control template, wherein the second primer comprises a nucleotide sequence that is complementary to the nucleotide sequence at a 3' end of the elongated extension product.

14. A method for monitoring the effectiveness of treatment of a subject with an agent that inhibits telomerase activity, said method comprising:
   obtaining a pre-administration sample from the subject prior to administration of the agent;
   detecting a level of telomerase activity in the pre-administration sample using the method of claim 1;
   obtaining one or more post-administration samples from the subject;
   detecting the level of telomerase activity in the post-administration samples using the method of claim 1; and
   comparing the level of telomerase activity in the pre-administration sample with the level of telomerase activity in the post-administration sample or samples.

15. A method for detecting and quantifying telomerase activity in a biological sample, the method comprising the steps of:
   incubating the biological sample with a reaction mixture comprising a first primer and nucleoside triphosphates under conditions suitable for a telomerase to produce an extension product from the first primer, said extension product comprising a telomeric repeat sequence at a 3' end;
   incubating said extension product with a template-independent terminal transferase or a template-independent ligase to produce an elongated extension product having a polyadenylate sequence at the 3' end;
amplifying the elongated extension product using a second primer in a real-time polymerase chain reaction; and
quantifying the amplified extension product using a control template, wherein said second primer comprises a sequence complementary to a junction of the telomeric repeat sequence and the polyadenylate sequences at the 3' end of the elongated extension product.

* * * * *

UNITED STATES PATENT AND TRADEMARK OFFICE
CERTIFICATE OF CORRECTION

| | | |
|---|---|---|
| PATENT NO. | : 7,390,621 B2 | Page 1 of 1 |
| APPLICATION NO. | : 10/534978 | |
| DATED | : June 24, 2008 | |
| INVENTOR(S) | : Zhuangwu Li et al. | |

It is certified that error appears in the above-identified patent and that said Letters Patent is hereby corrected as shown below:

Title Page; item (75);

First inventor name spelling from Zhunagwu Li to -- Zhuangwu Li --

Signed and Sealed this
Fourth Day of January, 2011

David J. Kappos
*Director of the United States Patent and Trademark Office*

SEQUENCE LISTING

```
<160> NUMBER OF SEQ ID NOS: 4

<210> SEQ ID NO 1
<211> LENGTH: 6
<212> TYPE: DNA
<213> ORGANISM: Homo sapiens

<400> SEQUENCE: 1 ttaggg                                                              6

<210> SEQ ID NO 2
<211> LENGTH: 68
<212> TYPE: DNA
<213> ORGANISM: Artificial
<220> FEATURE:
<223> OTHER INFORMATION: Synthetic telomerase template

<400> SEQUENCE: 2
aatccgtcga gcagagttag ggttagggtt agggttaggg ttagggttag ggttagggtt     60
agggttag                                                            68

<210> SEQ ID NO 3
<211> LENGTH: 18
<212> TYPE: DNA
<213> ORGANISM: artificial
<220> FEATURE:
<223> OTHER INFORMATION: synthetic PCR primer

<400> SEQUENCE: 3
aatccgtcga gcagagtt                                                 18

<210> SEQ ID NO 4
<211> LENGTH: 30
<212> TYPE: DNA
<213> ORGANISM: Artificial
<220> FEATURE:
<223> OTHER INFORMATION: synthetic PCR primer

<400> SEQUENCE: 4
gcgcggctta cccttaccct taccctaacc                                    30
```